United States Patent [19]

Clement et al.

[11] Patent Number: 5,021,602

[45] Date of Patent: Jun. 4, 1991

[54] REACTIVE COMPOUNDS CONTAINING PERFLUOROCYCLOBUTANE RINGS

[75] Inventors: Katherine S. Clement; David A. Babb; Bobby R. Ezzell, all of Lake Jackson, Tex.

[73] Assignee: The Dow Chemical Company, Midland, Mich.

[21] Appl. No.: 364,686

[22] Filed: Jun. 9, 1989

[51] Int. Cl.$^5$ .......................................... C07C 327/00
[52] U.S. Cl. ................................. 558/230; 568/645;
568/669; 568/329; 568/381; 568/442; 568/420;
568/3; 568/56; 560/357; 560/355; 560/358;
560/123; 560/60; 558/445; 558/251; 562/853;
562/472; 562/505; 564/442; 564/453; 564/454;
564/455; 552/6
[58] Field of Search .......................... 528/86; 526/243;
568/669, 645, 329, 381, 442, 420, 3, 56;
525/276, ; 560/357, 355, 358, 60, 123; 558/230,
251, 445; 562/853, 472, 505; 564/442, 453, 454,
455; 552/6

[56] References Cited

U.S. PATENT DOCUMENTS

| | | |
|---|---|---|
| 2,404,374 | 10/1951 | Harmon . |
| 2,671,799 | 3/1954 | Miller . |
| 2,848,504 | 8/1958 | Dixon . |
| 2,922,823 | 7/1960 | Tarrant . |
| 2,958,685 | 11/1960 | Eleuterio . |
| 2,982,786 | 5/1961 | McCane . |
| 3,022,356 | 6/1962 | Nooy . |
| 3,111,509 | 11/1963 | Folt . |
| 3,114,778 | 12/1963 | Fritz, et al. |
| 3,277,068 | 10/1966 | Wall et al. . |
| 3,303,145 | 2/1967 | Carlson . |
| 3,310,606 | 3/1967 | Fritz . |
| 3,316,312 | 4/1967 | McCane et al. . |
| 3,505,411 | 4/1970 | Rice . |
| 3,549,606 | 12/1970 | Gash . |
| 3,682,876 | 8/1972 | Anderson et al. . |
| 3,696,154 | 10/1972 | Anderson |
| 3,840,603 | 10/1974 | Anderson et al. . |
| 3,900,380 | 8/1975 | Anderson et al. . |
| 3,926,989 | 12/1975 | Rebsdat et al. . |
| 4,154,753 | 5/1979 | Fielding . |
| 4,377,711 | 3/1983 | Rico et al. . |
| 4,423,249 | 8/1983 | Carl et al. . |

FOREIGN PATENT DOCUMENTS

| | | |
|---|---|---|
| 1126554 | 9/1968 | United Kingdom . |
| 1185564 | 3/1970 | United Kingdom . |
| 8602072 | 4/1986 | WO |
| 303292 | 2/1989 | EPO |

OTHER PUBLICATIONS

Coffman, Barrick, Cramer and Raasch in J. Amer. Chem. Soc. vol. 71 (1949) pp. 490–496.
Chemical Abstract 110:181626 of EP 293,856 Henne and Ruh in J. Amer. Chem. Soc, 69, 279–281 (1947).
Maurice Prober in J. Amer. Chem. Soc., 75, 968–973 (1953).
Hauptschein et al. in J. Amer. Chem. Soc., 79 2549–2553 (1957).
Miller et al., in J. Amer. Chem. Soc., 83, 1767–1768 (1961).
Brown et al., in J. Poly. Sci. Part A-1, vol. 3, (1965) pp. 1641–1660.
Brown et al., in J. Poly. Sci. Part A-1, vol. 34 (1966) pp. 131–1140.
Banks, et al., in J. Chem. Soc. (C), 22 (1966) pp. 2051–2052.
Sharkey in Fluorine Chem. Rev. 2, 1–53 (1968).
Crawford in J. Chem. Soc. (C), 1967 pp. 2395–2396.
Hodgdon and Macdonald in J. Poly. Sci. Part A-1, vol. 6, (1968) pp. 711–717.
Chambers in Fluorine in Organic Chemistry, John Wiley, New York, (1973) pp. 173–191 and 199–208.
Rico and Waselman in J. Fluorine Chemistry, 20 (1982) 759–764.
Heinze and Burton in J. Org. Chem. 1988, 53, 2714–2720.
A.A. Glazkov et al. Bulletin of the Academy of Sciences of the USSR Vol. 37, no. 10 part 2.
P. Tarrant et al. J. Org. Chem. Vol. 31, no. 4, 1966 pp. 1143–6.
Chemical Abstract 105:171569h
Chemical Abstract 59:8879c
Chemical Abstract 77:34091k

*Primary Examiner*—Lewis T. Jacobs
*Assistant Examiner*—Thomas McDonald, Jr.

[57] ABSTRACT

Novel compounds have at least one perfluorocyclobutane ring and at least two functional groups suitable for forming condensation polymers. Preferably the compounds have a structures represented by Formula II:

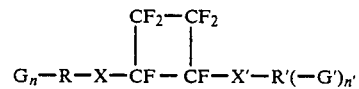

wherein R and R' independently represent optionally inertly substituted groups; X and X' represent any molecular structures which link R and R' with the perfluorocyclobutane ring; n and n' are the number of G and G' groups, respectively; and G and G' independently represent any reactive functional groups or any groups convertible into reactive functional groups. The compound are preferably prepared by a process of thermally dimerizing trifluorovinyl compound to form a compounds of Formula I

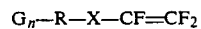

$$G_n\text{—}R\text{—}X\text{—}CF\!=\!CF_2$$

wherein G represents G' or G' in Formula II; X represents X or X' of Formual II; and n represents n or n' of Formula II, to form a compound having a perfluorocyclobutane group.

17 Claims, No Drawings

REACTIVE COMPOUNDS CONTAINING PERFLUOROCYCLOBUTANE RINGS

This invention relates to compounds having at least one perfluorocyclobutane group and at least two other functional groups and to polymeric compositions prepared from such compounds.

Perfluorocarbon and perfluoroalkylether polymers have desirable surface and electrical properties of high temperature stability and low dielectric constant, but generally lack the mechanical strength of known polymers, particularly engineering thermoplastics, such as commercial polycarbonates, polyesters, polyamides, and polyethers. One of the few ways of incorporating fluorocarbon character into engineering thermoplastics is by the use of molecules containing a perfluoroisopropylidene group joining two aromatic rings, each of which contains at least one reactive group, generally a hydroxyl or amino group to provide the means for condensation polymerization. It would be desirable to have monomers which provide other fluorocarbon functionality for the polymer backbone and which also offer more versatile functionality for condensation.

While difunctional compounds having fluorocarbon connecting moieties are known in the prior art, they are limited by both the method of preparation as well as the functional groups inherent in their synthesis. Such compounds are generally prepared from hexafluoroacetone by condensation with phenol or aniline. Resulting difunctional materials, or monomers, are, thus, limited to nucleophilic phenols and aromatic amines. It would be desirable to have a more general synthesis and a class of new monomers having both nucleophilic or electrophilic or mixtures thereof reactivity.

SUMMARY OF THE INVENTION

In one aspect, the invention is a compound having at least one perfluorocyclobutane ring and at least two reactive functional groups.

In another aspect, the invention is a process for preparing a compound of Formula II:

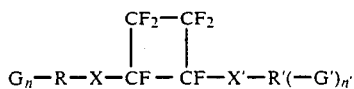

wherein R and R' independently represent optionally inertly substituted groups; X and X' represent any molecular structure which link R and R' with the perfluorocyclobutane ring; n and n' are the number of G and G' groups, respectively: and G and G' independently represent any reactive functional groups or any groups convertible into reactive functional groups comprising the step of thermally dimerizing compounds of Formula I:

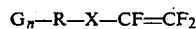

wherein G represents G or G' in Formula II; X represents X or X' of Formula II; and n represents n or n' of Formula II, to form a compound of Formula II.

In another aspect, the invention is a polymer which is the reaction product of a first compound having at least one perfluorocyclobutane ring and at least two functional groups and at least one second compound having at least two functional groups reactive with the functional groups of the first compound.

The present invention provides a general synthesis and a class of new monomers having a variety of nucleophilic and/or electrophilic reactivity.

DETAILED DESCRIPTION OF THE INVENTION

The invention includes compounds having at least one perfluorocyclobutane ring and at least two functional groups, said functional groups preferably being reactive functional groups, more preferably suitable for forming addition or condensation polymers; but alternatively being functional groups suitable for conversion into reactive functional groups. The functional groups are attached directly to the perfluorocyclobutane ring or, preferably indirectly via some linking structure thereto. The preferred compounds have structures represented by Formula II. wherein R and R' independently represent optionally inertly substituted groups; X and X' represent molecular structures which link R and R' with the perfluorocyclobutane ring: n and n' are the number of G

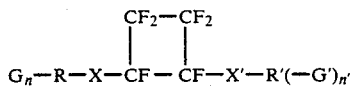

and G' groups, respectively, and preferably are independently integers of from 1 to about 4, more preferably from 1 to about 2 most preferably 1: and G and G' independently represent any reactive functional groups or any groups convertible into reactive functional groups, preferably any functional group suitable for reaction with di- or poly-functional compounds to form polymers. Alternatively, G and/or G' is a group suitable for chemical conversion into a functional group suitable for reaction to form a polymer.

G and G' are preferably independently selected from the group consisting of reactive functional groups including hydroxyl groups (both alcoholic and phenolic) and esters thereof, carboxylic acid groups, thiocarboxylic acid groups, thiocarboxylic and carboxylic esters, preferably lower alkyl esters of from one to about 12 carbon atoms, such as methyl and ethyl esters, acyl halides such as chlorides, isocyanates, acyl azides, acetyl groups, trihaloacetyl groups, primary or secondary amines, sulfide groups, sulfonic acid groups, sulfonamide groups, ketones, aldehydes, epoxy groups, primary or secondary amides, halo groups (e.g. chloro, bromo, iodo, and fluoro groups), nitro groups, cyano groups, anhydrides, imides, cyanate groups, vinyl, allyl, acetylene groups; silicon-containing substituents such as alkyl silanes, siloxanes, chlorosilanes, phosphorus-containing groups such as phosphines, phosphate, phosphonate, boron-containing groups such as boranes; and groups convertible into reactive functional groups including esters: trihalomethyl groups; alkoxy groups, alkyl groups when R is aromatic said alkyl and alkoxy groups preferably containing from about 1 to about 12 carbon atoms; and the like. More preferably, for ease in preparation of the compounds and polymers thereof, G and G' are independently selected from hydroxyl groups and esters thereof, carboxylic or thiocarboxylic acid ester groups, carboxylic acid groups, acyl chlorides, isocyanates, acetylenic groups, alkoxy groups alkyl groups when R is aromatic, and primary or secondary amines. Most preferably, for ease in preparation of the compounds and polymers thereof, G and G' are the same and are selected from hydroxyl and esters thereof, carboxylic acid ester groups, carboxylic acid groups, acyl chlorides, isocyanates, acetylenic groups, and primary or secondary amines.

X and X' are preferably independently a linking structure such as bonds, oxygen atoms, carboxylic and thiocarboxylic ester groups, other sulfur containing structures including sulfides and sulfones, perfluoroalkylenes, perfluoroalkylene ethers, alkylenes, acetylenes, phosphorus containing groups such as phosphines, carbonyl and thiocarbonyl groups; seleno; telluro; nitrido (N→O): silicon-containing groups such as silanediyl, trisilanediyl tetrasilanetetrayl, siloxanediyl, disiloxanediyl, trisiloxyl, trisilazanyl, or silylthio groups: boron-containing groups such as boranediyl or methylboranediyl groups; a combination thereof, or any other group which is inert and which molecularly links R or R' to a perfluorocyclobutane ring. By inert it is meant that a structure does not undesirably interfere with subsequent reactions of the compound, e.g. formation of a polymer. For ease of preparation, X is preferably the same as X', and both are preferably selected from oxygen or sulfur groups including sulfoxide and sulfone groups. In the preferred process for forming the compounds of the present invention, at least one of X and X' is preferably not a bond, more preferably neither X nor X' is a bond.

Preferably, X and X' are independently selected from the group consisting of groups having at least one non-carbon atom between the perfluorocyclobutane ring and R or R', such as groups containing oxygen, sulfur, selenium atoms, tellurium atoms, silicon, boron, phosphorus or nitrogen between R or R' and the perfluorocyclobutane ring, e.g. oxygen atoms, sulfur atoms, (thio) carboxylic ester groups, phosphines, (thio) carbonyl groups, seleno, telluro, silanediyl, trisilanediyl, trisilazanyl or silylthio, boranediyl groups. Preferred groups have S, O, Si, N or P, more preferably S, O, or Si between R and the perfluorocyclobutane ring, such as carbonyl, thiocarbonyl, sulfone, sulfoxy, silanediyl, amines (optionally inertly substituted), oxygen or sulfur atoms. Most preferably there is a single atom other than carbon; even more preferably it is oxygen or sulfur, among those groups preferably an ether or sulfide linkage, because monomers having such linking structures advantageously form perfluorocyclobutane groups at lower temperatures than are needed with such groups as perfluoroalkyl groups and are more stable than monomers where the precursor perfluorovinyl group is attached directly to R or R', particularly when R or R' is aromatic. Monomers having such linking structures are also relatively easily prepared.

When there are carbon-containing structures associated with X, X', G' or G, such as in ester groups, siloxane groups and the like, those carbon containing structures suitably have any number of carbon atoms, but preferably have from about 1 to about 50, more preferably from about 1 to about 12 carbon atoms.

R and R' are suitably any inert group which facilitates formation of perfluorocyclobutane rings and/or imparts desirable physical properties to polymers or oligomers prepared from compounds of Formula II, most preferably a hydrocarbyl group, (that is an inert group having at least one carbon atom bonded to a hydrogen atom, such as methylene, phenylene, or pyridinyl group). For the purpose of imparting desirable physical properties to polymers, R and/or R' preferably each contain at least one carbon atom. (Preferably, the carbon atom is in the molecular chain between X and G (or X' and G') because compounds having at least one carbon atom between those groups tend to have desirable stability and to produce polymers having desirable physical properties. Alternatively, the carbon atom is in a side chain: for instance, —R— can be —N(CH$_3$)—, —N(CH$_2$CH$_3$)— —P(CH$_3$)—, —P(CH$_2$CH$_3$)— and the like. The carbon atoms(s) in R or R' are suitably in aliphatic, cycloaliphatic, aromatic, heterocyclic groups and the like and combinations thereof. Additionally, R and R' optionally contain groups or have substituents which are inert, that is which do not undesirably interfere with the formation of perfluorocyclobutane rings from perfluorovinyl groups or interfere in subsequent reactions. Inert substituents include ether, carbonyl, ester, tertiary amide, carbonate, sulfide, sulfoxide, sulfone, nitrile, alkyl phosphonate, tertiary amine, alkyl phosphate, alkyl silyl, chlorine, bromine, fluorine, alkyl, arylalkyl, alkylaryl, cycloalkyl, aromatic, heterocyclic, alkoxyl, aryloxy groups and the like, which inert substituents are suitably in any position on R or R'. Carbon-containing inert substituents on R or R' preferably contain from about 1 to about 50, more preferably from about 1 to about 12 carbon atoms because of the stability and ease of working with monomers of lower molecular weight. R and R' each, including inert substituents, preferably has a molecular weight (MW) of from about 14 to about 20,000, more preferably from about 75 to about 15,000 and most preferably from about 75 to about 5,000. These ranges include monomeric and oligomeric R and R' groups. In the case of monomers which are other than oligomeric, R and R' preferably have from about 1 to about 50, more preferably from about 6 to about 25, carbon atoms because molecular weights above this reduce the contribution to properties made by the fluorine-containing substituents when R and R' are alkyl or aromatic hydrocarbon groups not containing substantial fluorine.

Preferably, for polymers having good plastic properties such as tensile strength and flexibility, at least one carbon atom of R and/or R' is in the molecular chain between X and G (or X' and G') and is part of an aromatic nucleus. Aromatic groups are desirable because of improved physical properties of the polymers and ease of manufacture of the monomers. For both ease of manufacture of the monomer and stability of the trifluorovinyl precursor, when R or R' is aromatic, each of X and X' is preferably a group having only non-carbon atoms, more preferably one non-carbon atom, most preferably one non-carbon atom is sulfur or oxygen between R or R' and the perfluorocyclobutane group. The aromatic group can be any molecular structure having aromatic character, advantageously having at least one six membered aromatic ring, suitably having any number of such six-membered rings fused together or connected by bonds or linking structures. Each of R and R' preferably has from about 1 to about 50 such rings, more preferably from about 1 to about 10 rings, more preferably containing from about 6 to about 25 carbon atoms, most preferably each of R and R' has at least 1 to about 4 aromatic rings to impart properties such as hardness and/or stiffness to a polymer. The aromatic fragment is suitably unsubstituted or inertly substituted. Inert substituents on an aromatic R or R' include, for instance, the inert substituents listed for R generally. Exemplary aromatic molecular fragments include, for instance, perchlorophenylene, phenylene, biphenylene, naphthylene, dichlorophenylene, nitrophenylene, p,p'(2,2-diphenylene propane) [—C$_6$H$_4$—C(CH$_3$)$_2$—C$_6$H$_4$]; p,p'-(2,2-diphenylene-1,1,1,3,3,3 hexafluoropropane) [—C$_6$H$_4$—C(CF$_3$)$_2$—C$_6$H$_4$—], preferably biphenylene; phenylene; 9,9'-diphenylfluorene, oxydiphenylene: thiodiphenylene; 2,2-diphenylene propane; 2,2'-diphenylene, 1,1,1,3,3,3-hexafluoropropane:; 1,1-diphenylene-1-phenyl ethane; naphthalene; and anthracene. Molecular weights of aromatic ring containing polymers are preferably at least about 10,000. Such aromatic groups are preferably present because they generally impart high temperature glass transition properties (Tg) and good mechanical strength (e.g. as measured by differential scanning calorimetry (DSC) and tensile/flexural tests) to the polymer.

More preferably, at least one aromatic carbon atom of R (or R') is bonded directly to X (or X'), most preferably both X and X' are bonded to aromatic carbon atoms of R (and R') because perfluorovinyl groups bonded to X (or X'), said X (or X') being bonded to aromatic groups are generally more reactive in forming perfluorocyclobutane rings.

In the preferred method of preparing the compounds of the present invention some specific combinations of X, X', R and R' are especially preferred: when R or R' is aromatic, the corresponding X or X' is preferably other than a bond, more preferably neither X nor X' is a bond, because attachment of perfluorovinyl groups directly to an aromatic group renders the perfluorovinyl groups more thermally and oxidatively unstable than when said groups are attached, for instance to oxygen or sulfur. When R or R' is a perfluoroalkyl group or a perfluoroalkylether group, at least one of X or X' is preferably other than a bond, most preferably neither X nor X' is a bond, because perfluorovinyl groups linked directly to perfluoroalkyl groups require temperature in excess of about 300° C. to dimerize and are subject to isomerization.

Compounds of Formula II are preferably formed by thermally dimerizing perfluorovinyl compounds having at least one reactive functional group or a group suitable for conversion into such a functional group. More preferably, the perfluorovinyl compounds have structures represented by Formula I:

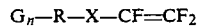
G$_n$—R—X—CF=CF$_2$ wherein R represents an optionally substituted group: X represents any molecular structure which links R and a perfluorovinyl group; n is the number of G groups, preferably an integer of from 1 to about 4, more preferably from 1 to about 2, most preferably 1; and G represents any reactive functional group or any group convertible into a reactive functional group, preferably any functional group suitable for reaction with di- or polyfunctional compounds to form polymers, which functional group (G) is, more preferably, insufficiently nucleophilic to react undesirably with perfluorovinyl groups at room temperature (e.g. 25° C.), most preferably at temperatures used in subsequent reactions of the compound. Alternatively, G is a group suitable for chemical conversion into a reactive functional group.

G is preferably selected from the group consisting of functional groups including hydroxyl groups (both alcoholic and phenolic) and esters thereof, carboxylic acid groups, acyl halides such as chlorides, isocyanates, acetyl groups, trihaloacetyl groups, sulfide groups, sulfonic acid groups, sulfonamide groups, ketones, aldehydes, epoxy groups, primary or secondary amides, halo groups (e.g. chloro, bromo, iodo, and fluoro groups), nitro groups, cyano groups, anhydrides, imides, and esters including thiocarboxylic and carboxylic esters, preferably lower alkyl esters such as methyl and ethyl esters, trihalomethyl groups including trichloromethyl groups, silicon-containing substituents such as alkyl silanes, siloxanes, chlorosilanes, phosphorus-containing groups such as phosphines, phosphate, phosphonate, boron-containing groups such as boranes, alkoxy groups preferably containing from about 1 to about 12 carbon atoms, and alkyl groups preferably containing from about 1 to about 12 carbon atoms when R is aromatic and the like. Most preferably, for ease in preparation of the polymers from compounds of Formula II G is selected from hydroxyl and esters thereof carboxylic or thiocarboxylic acid ester groups, carboxylic acid groups, acyl chlorides, isocyanates, alkyl groups when R is aromatic; and alkoxy groups.

In many cases it is preferred to have G of Formula I as a group that is later converted to a reactive group after dimerizing to compounds of Formula II. Temperatures necessary for dimerization are sufficiently high to cause undesirable side reactions in some cases. Examples include G (of Formula I) being sufficiently nucleophilic to react with trifluorovinyl groups, e.g. amines. To prepare a compound of Formula II wherein G and/or G' are amine it is preferred to dimerize a compound of Formula I where G is nitro or amide and then convert, by reduction or hydrolysis, to amine after the dimerization. Another example is where G or G' of Formula II is ethynyl, i.e. a group known to cycloaromatize. In this case, as shown in the examples of the invention, it is convenient to dimerize the compound of Formula I where G is ethyl and then convert to ethynyl after dimerization. Other similar manipulations would be obvious to those skilled in the art and familiar with general functional group reactivities.

Preferred structures for X and R are as for X and R in Formula II. More detail regarding the compounds of Formula I and their preparation is given in U.S. application Ser. No. 364,666 filed June 9, 1989, which is incorporated herein in its entirety.

Compounds of Formula II wherein at least one of R', X', and G' are different from the corresponding R, X, and G, but selected from the same categories as defined for R, X, and G, are prepared by cross dimerizing compounds of Formula I, wherein at least one R, X, and G are replaced with R', X', and G', with compounds of Formula I, having R, X, and G.

The perfluorovinyl compounds are preferably thermally dimerized by heating the compounds to a temperature and for a time sufficient to form perfluorocyclobutane rings. Temperatures suitable for forming perfluorocyclobutane rings differ with the structure of the perfluorovinyl compound. In general, temperatures above about 40° C. are suitable for formation of perfluorocyclobutane rings, preferably the temperature is above about 50° C., more preferably above about 100° C., because these temperatures result in formation of the rings at successively faster rates. Dimerizations are preferably carried out by stirring and heating the neat perfluorovinyl compounds under nitrogen to approximately 195° C. for several hours. Temperatures above about 450° C. are preferably avoided because perfluorocyclobutane rings are thermally unstable at such temperatures.

Preferably, especially when the perfluorovinyl compounds are capable of addition polymerization, like formation of polytetrafluoroethylene, conditions conducive to free radical polymerization, e.g. presence of oxygen, ozone, peroxygen compounds and other free radical generating compounds, are avoided so that the perfluorovinyl groups will dimerize into perfluorocyclobutane groups rather than addition polymerizing. Compounds known in the art for stabilization against free radical polymerization such as limonene are alternatively used. Similarly, especially when the perfluorovinyl groups are capable of addition polymerization in the presence of anions or cations, compounds which supply such anions or cations are avoided. For instance, fluoride (e.g. from carbonyl fluorides), chloride, hydroxide, phenoxide ions and the like are preferably avoided. To avoid such compounds as carbonyl fluorides, oxidative conditions such as presence of oxygen, hypochlorite, dichromate, permanganate and the like are preferably avoided because perfluorovinyl groups are known to oxidize to form carbonyl fluorides. Perfluorovinyl ethers, thioethers, sulfones, sulfoxides and the like are relatively stable with regard to addition polymerization and oxidation; and, therefore, such precautions are generally unnecessary when these perfluorovinyl compounds are used.

Advantageously, the perfluorovinyl compounds are stirred while they are heated. Perfluorovinyl compounds or admixtures thereof are preferably neat or, alternatively are in admixture with other materials such as in solution, in emulsion, in dispersions or in any other form in which perfluorovinyl compound molecules can be contacted with one another to form a dimer. Liquid admixtures are advantageous for maintaining contact between perfluorovinyl compound molecules such that dimers are formed.

Dimerizing suitably takes place at any pressure. Pressures of about one atmosphere are generally preferable for convenience when the perfluorovinyl compounds and any solvents and/or dispersing media remain liquid at the temperatures used for dimerizing. Other pressures are also suitably used, and are especially useful when the perfluorovinyl compounds have boiling points below the optimum dimerization range. Unreacted perfluorovinyl compounds along with any tetrafluoroethyl byproducts are preferably removed from the high boiling dimer by distillation at reduced pressure. The dimer is conveniently then distilled under high vacuum for further purification. Alternatively, other purification methods within the skill in the art are used.

Additional detail regarding formation of perfluorocyclobutane rings is given in copending U.S. application Ser. No. 364,667 filed June 9, 1989, pending which is incorporated herein in its entirety.

Compounds having a perfluorovinyl group and a functional group are advantageously formed by chemically reacting a compound having a perfluorovinyl group with a compound having a suitable functional group or a molecular structure suitable for conversion to a functional group (e.g. by techniques disclosed in such references as Antonucci, High Polymers, Vol. XXV, "Fluoropolymers," Chapter 2, "The Synthesis and Polymerization of Fluorostyrenes and Fluorinated Vinyl Phenyl Ethers," pp. 33–82 (1972); or, preferably by forming a compound having a functional group or a molecular structure suitable for conversion to a functional group and a molecular structure suitable for conversion to a perfluorovinyl group, then converting that structure to the perfluorovinyl group. In either case, a molecular structure suitable for conversion to a functional group is then converted to the functional group.

Preferably, the process comprises the steps of:

(a) preparing a 2-halotetrafluoro compound of Formula III:

$$Q-CF_2-CF_2-X-R-(-G'')_n$$

wherein X, R and n are as previously defined for X, X', R, R' and n in Formula I; Q is bromine, chlorine or iodine: preferably bromine or iodine, most preferably bromine; and G" is a functional group G, as previously defined, or a functional group suitable for conversion into G or G'; and (b) chemically modifying group G" to produce functional group G or G';

(c) dehalogenating the 2-halotetrafluoro compound to form the corresponding trifluorovinyl compound. Step (b) optionally precedes or follows step (c), or steps (b) and (c) are simultaneous, generally depending on the relative ease of the reactions required and the relative sensitivity of the 2-halotetrafluoro group or the trifluorovinyl group to the chemical reactions required for step (b).

For step (a), compounds of Formula III are suitably prepared by any method within the skill in the art such as by processes taught by Rico et al. in U.S. Pat. No. 4,377,711; by Carl et al. in U.S. Pat. No. 4,423,249 which patents are incorporated by reference herein; by Antonucci in High Polymers Vol. XXV, ed. Walls, Wiley Interscience (1972) and references therein; by Xingya in Tetrahedron Letters, 1984, 25 (43), 4937–4940 and references therein.

Preferably they are prepared by a process including the steps of:

(1) forming a salt having an anion represented by Formula IV:

$$-X-R-(G'')n$$

(2) reacting the salt with a 1,2-dihalo-1,1,2,2-tetrafluoroethane wherein the halo (halogen) groups are as defined for Q in Formula III, but at least one of the halo groups is bromine or iodine.

For step (1), salts having anions of Formula IV are suitably formed by any method which associates a metal cation with such an anion, for instance replacing hydrogen atoms of compounds such as those of Formula V:

$$HX-R-(G'')n$$

with metal cations. Suitable methods include reaction with bases such as sodium hydroxide or potassium hydroxide when the compound has an acidity sufficiently high to react with a hydroxides, such as when R is aromatic carbocyclic or aromatic heterocyclic. Compounds of lower acidity are reacted, for instance, with metals such as sodium or their hydrides or metal salts of carbon acids. Among hydroxides, potassium hydroxide is generally preferred because potassium salts of alkoxides or aryloxides are more reactive than are lithium or sodium salts, for instance, sufficient hydroxide or metal to form the salt is used, preferably at least about 1.0 equivalents of hydroxide of metal per equivalent of compound of Formula V. Suitable temperatures and pressures are determined without undue experimentation and are conveniently atmospheric pressure and a temperature maintained below about 140° C. to avoid ring halogenation when there is an aromatic ring in the compound. Temperatures are preferably from about −10° C. to about 125° C. for an aromatic compound (R is aromatic) and of from about −25° C. to about 25° C. for an alkyl compound.

Suitably, both the compound of Formula V and the hydroxide are slurried or dissolved in an easily removable medium such as methanol before reaction for convenience in mixing the reactants. Alternatively, and preferably, the hydroxide is mixed directly into a solution of the compound of Formula V in a solvent such as methanol, a glyme, water or mixtures thereof.

Alteratively, salts may be formed by reaction of compounds of Formula V with metals or their hydrides such as Group I metals including sodium and potassium or any metal or its hydride which reacts to form salts with compounds of Formula V at temperatures of from about −25° C. to about 150° C. These reactions are particularly useful when H—X—R—(G")n is unreactive toward metal hydroxides. Use of metals and their hydrides is within the skill in the art and is found, for instance in Fieser and Fieser, Reagents for Organic Synthesis, Wiley-Interscience, New York (1967).

Although it is generally preferable for convenience, to maintain reactants in a slurry or solution for subsequent reaction, any liquid medium, e.g. methanol or glyme is suitably, alternatively, removed before the next reaction step. Removal of protic media is necessary. Removal is within the skill in the art. Methanol, for instance is conveniently removed by rotary evaporation followed by heating to about 100°–140° C. under vacuum until the salt is dry. Other media are conveniently removed, for instance, by filtration, spray-drying particularly of water solutions, or freeze-drying.

For step (2), the salt is then reacted with a 1,2-dihalo-1,1,2,2-tetrafluoroethane which is commercially available.

The dihalotetrafluoroethane has a structure represented by Formula VI

Q—CF$_2$—CF$_2$—Q' wherein Q and Q' represent halogens other than fluorine. Q and Q' are preferably selected such that the tetrafluoroethane reacts readily with the anion (preferably of Formula IV), leaving one halogen (Q or Q'), and that halogen is later readily eliminated to form a perfluorovinyl group. Q and Q' are, therefore, preferably selected from Cl, Br, and I and at least one of Q and Q' is Br or I: more preferably Q and Q' are independently Br or I: most preferably Q and Q' are Br. 1,2-dibromo-1,1,2,2-tetrafluoroethane is preferred because it is liquid at room temperature, stable, and readily available.

The 1,2-dihalotetrafluoroethane is preferably reacted with the salt in a liquid reaction medium which is, for instance, suitably a solution or slurry of the salt in an aprotic solvent such as an ether, (e.g. diethyl ether), dioxane, dimethyl sulfoxide (DMSO), glyme, diglyme, tetraglyme, tetrahydrofuran, dimethyl formamide (DMF), or acetonitrile. The glymes, DMSO, and DMF are preferred, with DMSO most preferred but DMF most preferred at low temperatures below which DMSO begins to freeze. When the reaction medium is a slurry it is preferably stirred sufficiently to maintain the slurry and contact between the dihalotetrafluoroethane and the salt. Sufficient solvent to homogeneously disperse both the dihalotetrafluoroethane and the salt is used, preferably from about 1 to about 99, more preferably from about 25 to about 75 weight percent solvent relative to weight of salt, for convenience. Sufficient salt is reacted with the dihalotetrafluoroethane to form a predetermined degree of substitution: preferably from about 0.1 to about 10.0 equivalents of salt per equivalent of dihalotetrafluoroethane is supplied, more preferably from about 0.75 to about 1.1 equivalent of salt. The dihalotetrafluoroethane is preferably added as a liquid at room temperature or with cooling and/or pressure if necessary to maintain the liquid phase.

The reaction temperature is preferably maintained above −30° C. to achieve reaction at a convenient rate and below 125° C. to avoid by-products. More preferably the temperature is maintained between about −10° C. and about 125° C., most preferably between about 0° and about 125° when R is aromatic and X is —O—, —S—, -SO$_2$— or —SO—; most preferably between about −10° C. and about 25° C. when R is alkyl. These temperatures are preferably used at atmospheric pressure which is preferable for convenience. Alternatively sub- or super-atmospheric pressure is used and temperature adjustments within the skill in the art are made. The temperature of the reaction is also dependent on the nature of a substituent group. In general, electron donating substituents enhance the reaction, and cooling is necessary to keep the reaction temperature down. Electron donating substituents also activate the aromatic ring toward halogenation which can be a significant side reaction at elevated temperatures. The reactions are preferably run at the lowest temperature possible to prevent ring halogenation. Electron withdrawing substituents, however, retard the reaction and deactivate the ring toward halogenation. Reactions involving deactivated phenols are preferably heated to obtain a convenient reaction rate. The deactivated phenols can be heated much hotter than the activated phenols, because the deactivating groups also retard ring halogenation. In all cases the reaction is advantageously kept substantially free of protic materials, which are preferably at concentrations of less than about 0.1 weight percent, most preferably in no detectable concentrations. Protic materials can cause production of an undesirable side product (i.e. —OCF$_2$CF$_2$H instead of —OCF$_2$CF$_2$Br). Protic materials include water, alcohols, phenols and the like.

When aromatic ethers are formed, the ease of the reaction of a phenol salt and 1,2-dihalotetrafluoroethylene is correlatable to the pKa (acidity) of the parent phenol. The presence of an electron-withdrawing substituent retards the reaction, and decreases the pKa of a phenol: increasing temperatures are required to obtain ether formation. A comparison of the pKa's of substituted phenols and reaction temperature for ether formation is shown in Table 4.

TABLE 4

| Aromatic substituent | pKa (para) | Rxn Temp. °C. | pKa (meta) | Rxn Temp. °C. |
|---|---|---|---|---|
| —CH$_3$ | 10.26 | 0–20 | 10.00 | — |
| —OCH$_3$ | 10.2 | 0–20 | 9.65 | — |
| —CH$_2$CH$_3$ | 10.0 | 10–20 | 10.07 | 0–20 |
| —H | 9.99 | 20–25 | 9.99 | 20–25 |
| —F | 9.89 | — | 9.29 | — |
| —Cl | 9.43 | — | 9.1 | — |
| —Br | 9.34 | 65 | 9.03 | — |
| —CO$_2$— | 9.23 | 65 | 9.85 | — |

TABLE 4-continued

| Aromatic substituent | pKa (para) | Rxn Temp. °C. | pKa (meta) | Rxn Temp. °C. |
|---|---|---|---|---|
| —CO$_2$CH$_3$ | 9.2 | 65 | 9.8 | — |
| —C(O)CH$_3$ | 8.05 | 70–85 | 9.19 | — |
| —CN | 7.95 | — | — | — |
| —CHO | 7.62 | 75–85 | 9.0 | — |
| —NO$_2$ | 7.15 | >90 | 8.36 | — |

Some substituent groups, for example, ketones and aldehydes, are capable of forming by-products in the reaction with a dihalotetrafluoroethane. These reactive substituent groups are best protected (e.g. as acetals) prior to reaction. It is observed that meta-substituted phenoxides, in most case, react at lower temperatures than corresponding para-substituted phenoxides.

Reaction of a 1,2-dihalotetrafluoroethane and the salt forms a 2-halotetrafluoroethyl compound. The 2-halotetrafluoroethyl compound is either separated from the liquid media or slurry or is further reacted in the medium. Removal is by means within the skill in the art, such as by pouring the slurry into an equal volume of water and removing the product in a lower, oily layer which is then purified by vacuum distillation. If a liquid medium such as tetraglyme which does not completely dissolve in water is used, the product is conveniently distilled therefrom under vacuum. Otherwise, the product in a solvent such as a glyme (including multiple glymes such as diglyme and tetraglyme) is conveniently filtered from the precipitated salts, and isolated by distillation or used without purification in the dehalogenation reaction. It is preferable to remove the solvent if a different solvent is preferred for the dehalogenation reaction, also, any unreacted dihalotetrafluoroethane is preferably removed prior to dehalogenation to avoid production of by-products.

In step (c), the non-fluorine halogen atom and a fluorine atom are then eliminated from the product 2-halotetrafluoroethyl compound to form the perfluorovinyl compound. The elimination is suitably conducted by any effective means. Preferably a metallic reagent such as magnesium or zinc, (more preferably zinc) is reacted with the 2-halotetrafluoroethyl compound, preferably in a liquid medium such as the ones suitable for formation of the salt. Alternatively, some reactants are sufficiently liquid for convenient reaction in the neat form. More preferably, the 2-halotetrafluoroethyl compound is added to a hot (about 75°–140° C.) preferably about 110°–115° C. slurry of (preferably granular) zinc most preferably in a dry glyme, or other liquid medium which is aprotic. The reaction is exothermic and the temperature is regulated by the speed of the addition of reactants. Most preferably, the halotetrafluoroethyl compound is mixed with the metallic agent in a dry glyme and refluxed at about 85°–90° C. with stirring until the perfluorovinyl compound is formed, generally several hours, conveniently overnight. Better yields are generally observed in glymes. Zinc is preferred not only because of its effectiveness but also because few substituent groups (other than possibly nitro groups) on aromatic portions of the molecule react with zinc. Granular zinc is convenient to work with, but size has little effect on the reaction except that powdered zinc increases the reaction rate to a vigorous level. The zinc is preferably cleaned by washing with dilute acid (e.g. hydrochloric acid), rinsing with water and drying under vacuum. This method enhances initiation of the elimination reaction and accelerates the rate of that reaction.

Efficient stirring is important to avoid occluding the active metallic reagent in a heavy precipitate of metallic salts. Dehalogenation is exothermic, and if carried out at 110°–115° C., the addition rate of a dihalotetrafluoroethyl ether to the reaction mixture is preferably controlled to avoid overheating. It is preferable to adjust the rate of addition so that the reaction maintains itself at about 110°–115° C. without external heating.

After completion of the reaction, any precipitated materials, e.g. metal salts are removed, by methods within the skill in the art, conveniently by centrifugation because the precipitates are often very fine. If diglyme or tetraglyme or higher boiling solvent is used, the product is preferably fractionally distilled from the mixture. If glyme or a lower boiling solvent is used, the solvent is conveniently removed by rotary evaporation and the product perfluorovinyl compound is preferably purified by distillation.

Compounds of Formula II having a perfluorocyclobutane group and at least two functional groups are then prepared by (d) thermally dimerizing perfluorovinyl compounds having at least one reactive functional group or a group suitable for conversion to a functional group, and converting the suitable groups to the functional groups as appropriate. Thus, compounds of Formula II are formed by a process comprising steps (a) through (c) explained above and step (d). In the process, step (d) follows step (c), but step (b) optionally precedes or follows steps (c) or (d), depending on the relative sensitivity of the groups present to subsequent reactions. Determining suitable order of reaction steps is within the state of the art without undue experimentation.

For step (b), the perfluorovinyl compounds may contain functional groups as described for G and G' in Formulas I and II such as alkyl when R or R' is aromatic, alkoxy, halide, ester, acid, ketone, aldehyde, nitro, nitrile, alkylthio groups which do not react undesirably with the perfluorovinyl compound or interfere with formation of its dimer, the perfluorocyclobutane compound. Alternatively, the perfluorovinyl compound can have a molecular structure suitable for conversion to a functional group (G″ in Formula III). Conversion after dimer formation is preferred when the functional group for polymerization is reactive with a perfluorovinyl group or would undergo side reactions at dimerization temperatures. Exemplary of such groups are esters which are convertible to acid chloride by saponification followed by treatment with thionyl chloride according to the procedures disclosed by J. Cason *Org. Syn.*, Coll. Vol. 3, 169 (1955); methoxy groups which are convertible to hydroxy groups by treatment with NaI and Me$_3$SiCl in CH$_3$CN according to the procedures disclosed by Olah in *J. Org. Chem.* 1979, 44, 1247–1251; ethyl groups on perfluorocyclobutane compounds which are convertible to ethynyl groups by procedures detailed in examples of the invention; esters which are convertible to acid chloride and subsequent conversion to isocyanates by Curtius rearrangement according to the procedures disclosed by P. Smith in *Organic Reactions.* Vol. 3, p 337–449, Wiley, NY ed. Adams (1946); to amines by Curtius reaction according to the procedures disclosed by P. Smith in *Org. Reactions*, Vol. 3, p 337–449, ed. Adams, Wiley, NY (1946). Those skilled in the art are familiar with other such conversions. Examples of the invention provide additional detail with regard to useful conversions.

It is within the scope of the invention to form compounds of Formula II by dimerizing compounds not containing a functional group G, i.e. RXCF=CF$_2$, then reacting the dimer with appropriate chemical reagents to form G on the dimer, particularly when R is aromatic. Illustrative of the above technique is to first dimerize phenyl trifluorovinyl ether. Reaction of the dimer with various sulfur derivatives such as SO$_3$, SO$_2$F$_2$ or the like results in compounds of Formula 11 where G is a sulfonic acid or derivative. Nitration of the dimer results in compounds of Formula II wherein G is nitro. Reduction of the latter product results in compounds of Formula II wherein G is an amine. Numerous methods to achieve this embodiment of the invention and form compounds of Formula II are readily accomplished using chemical reactions within the skill in the art.

Compounds similar to compounds of Formula II, but having more than one perfluorocyclobutane group are readily prepared by the reaction of compounds of Formula I with monomers, oligomers or polymers of compounds having more than one trifluorovinyl group. Such compounds having more than one perfluorocyclobutane group preferably have at least two functional groups corresponding to the preferred G and G', and separations between G or G' and the perfluorocyclobutane rings corresponding to X or X' and R or R', all of Formula II. The preparation and polymerization of compound having more than one trifluorovinyl group are disclosed in copending applications Ser. No. 364,667, filed pending June 9, 1990 and Ser. No. 364,665, filed June 9, 1989 pending which are incorporated herein by reference in their entirety. Monomers, oligomers or polymers of compounds having more than one trifluorovinyl group are terminated with trifluorovinyl groups. Reactions of these compounds with compounds of Formula I under conditions disclosed herein for cyclodimerization of compounds of Formula I to form compounds of Formula II result in formation of terminal perfluorocyclobutane groups substituted with—X—R—G derived from Formula I.

Compounds of the present invention having more than one perfluorocyclobutane group are preferable in cases where more fluorocarbon character such as lower dielectric constant is desirable in the polymers produced from these compounds. In addition, these type compounds having more than one perfluorocyclobutane group are useful for introducing more flexibility in polymers than would be present using compounds of Formula II. This aspect is particularly true when highly crosslinked polymers are the final products, for example when G and/or G' is acetylenic or in compounds where n or n' is greater than 1. Preferably the compounds with more than one perfluorocyclobutane group have from about 2 to about 50, more preferably from about 2 to about 25 perfluorocyclobutane groups, depending on other molecular fragments therein and desired properties.

Compounds of the invention are suitable for reacting with other monomers having at least two functional groups reactive with the functional groups of the perfluorocyclobutane compounds to form polymers. Reaction conditions for forming the polymers are generally those suitable for use in forming polymers from compounds having the same functional groups as the compounds of the invention but not having a perfluorocyclobutane group. Such conditions are readily ascertained by those skilled in the art without undue experimentation, references for more detail in forming polymers include *Organic Polymer Chemistry* by K. J. Saunders, Chapman and Hall, London (1973). Additional detail relating to application of these general conditions to the compounds of the invention is found in the examples of the invention.

Polymers formed from compounds of the invention generally have properties of mechanical strength (e.g. as measured by ASTM D790-86) characteristic of the type of polymer, e.g. polyester, polycarbonate, polyamide, etc., produced and have properties of low dielectric constants characteristic of fluorocarbon polymers. For instance, polymers of the invention preferably have dielectric constants of at least about 2.0, more preferably of from about 2.0 to about 4.0 as measured by ASTM D150-87.

The polymers can generally be shaped by methods used for shaping polymers not having perfluorocyclobutane rings such as by injection molding, extrusion, casting and other methods within the skill in the art.

The following examples are offered to illustrate but not to limit the invention. In each case, percentages are by weight unless otherwise indicated. Examples (Ex.) of the invention are indicated numerically, while comparative samples (C.S.) are not examples of the invention and are indicated with letters.

In each case, gas chromatographic (GC) analyses are done on a Varian 3700 GC using a 30 m DB210 megabore column (commercially available from J&W Scientific) and a flame ionization detector. The conditions are: injector, 150° C.; detector, 250° C.; temperature program: 50° C. for 3 min, then increase 10° C./min to 180° C. and hold; initial column pressure 20 psig (pounds per square inch gauge). Proton nuclear magnetic resonance (NMR) spectra are taken on a EM-360 or T-60 (Varian) nuclear magnetic resonance spectrometer. Fluorine (19 F) NMR's are taken on a Varian EM-360 modified for 19F NMR using trifluoroacetic acid (TFA) as the external zero reference. The 19F NMR spectra of the 2-bromotetrafluoroethyl ethers appears as two triplets within the ranges of: (CF$_2$Br)—10.2 to −9 ppm (J approximately 7-9Hz) and (CF$_2$O) 7.8 to 9.5 ppm (J approximately 7-9Hz). The 19F NMR spectra of the trifluorovinyl ether appear as 3 doublets of doublets within the ranges of: (=CF, cis to F) 39 to 45 ppm, (J cis approximately 60 Hz, J gem approximately 100 to 107 Hz). (=CF, trans to F) 45 to 52 ppm, (J trans approximately 112 to 120 Hz, J gem approximately 100 to 107 Hz); (OCF) 55 to 60 ppm, (J trans approximately 112 to 120 Hz, J cis approximately 60 Hz). The 19F NMR spectra of the substituted perfluorocyclobutane rings appear as broad multiplets at 48 to 55 ppm. Infrared analyses are performed on a Beckman IR-33 or a FTIR (Fourier transform infrared spectrometer) to obtain spectra characteristic of the respective functional groups and characteristic of a perfluorovinyl group at about 1845 cm$^{-1}$. Thermal data are obtained on a Perkin-Elmer 7 Series Thermal Analysis System according to manufacturer's directions. Gas chromatography/mass spectrometry (GC/MS) is performed on a Finnigan 1020 using a 30 m RLS 150 capillary column. Conditions are varied to give the best combinations of retention time and resolution.

EXAMPLE 1

Preparation of Methyl 4-Trifluoroethenyloxybenzoate, Dimerization and Derivation to form 1,2-Bis (4-Chloroformylphenoxy)Hexafluorocyclobutane Methyl p-hydroxybenzoate is converted to its potassium salt by reaction with a stoichiometric amount of potassium hydroxide in methanol. The salt is isolated by evaporation and dried under vacuum. The dried salt is slurried in an equal weight of dry dimethyl sulfoxide. The mixture is stirred and heated to about 50° C. and a slight excess of 1,2-dibromotetrafluoroethane is added slowly. The reaction temperature is maintained at 60°-70° C. An efficient condenser is necessary to condense the dibromotetrafluoroethane. After addition is complete, the mixture is warmed for an additional hour, cooled and poured into an equal volume of water. The product (methyl 4-(2-bromotetrafluoroethoxy)benzoate) separates as a brown oil which is distilled under vacuum (85°-90° C., 0.3 torr) to yield a colorless oil (85-95% yield).

The bromotetrafluoroethyl ether is dehalogenated by combining it with a stoichiometric amount of granular zinc in glyme and refluxing overnight. After removal of the glyme by evaporation, the product, methyl 4-trifluoroethenyloxybenzoate, is distilled under vacuum (85°-90° C./8-10 torr, 85-100% yield).

The methyl 4-trifluoroethenyloxybenzoate is cyclodimerized by heating at 195° C. for several hours. The dimerized product, 1,2-bis(4-carbomethoxyphenoxy)hexafluorocyclobutane, is isolated by distillation (135°-150° C./0.025 torr, 97% yield, with the remainder being unreacted vinyl compound). The overall yield from methyl p-hydroxybenzoate is 80%.

The dimer is saponified to the diacid with 2.1 molar equivalents of sodium hydroxide in methanol. Upon acidification with concentrated hydrochloric acid the diacid precipitates and is filtered from the liquid as an insoluble white powder with a melting point above 300° C. Yields are quantitative. The diacid is converted to the diacid chloride by slurrying it in approximately a 6 molar equivalent of thionyl chloride and warming the mixture to 50°-75° C. The product diacid chloride is soluble in dichloromethane and is purified by dissolving the crude reaction product in dichloromethane and filtering the diacid chloride solution from unreacted diacid (which is insoluble). The product is identified by 19FNMR, HNMR and infrared (IR) spectra. IR 1790, 1755 cm$^{-1}$ (C=O), no CO$_2$H absorption.

EXAMPLE 2

Preparation of 4-Trifluoroethenyloxyanisole, Dimerization and Derivation to form 1,2-Bis(4-Hydroxyhpehenoxy)Hexafluorocyclobutane 4-Methoxyphenol is converted to its potassium salt by reaction with a stoichiometric amount of potassium hydroxide in methanol. The salt is isolated by evaporation and dried under vacuum. The dried salt is slurried in an equal weight of dry dimethyl sulfoxide. The mixture is stirred and cooled in an ice bath as a slight excess of 1,2-dibromotetrafluoroethane is added slowly to maintain the reaction temperature at <30° C. After addition is complete, the mixture is warmed to 50° C. for an additional hour, cooled and poured into an equal volume of cold water. The product, 4-(2-bromotetrafluoroethoxy)anisole, separates as a brown oil which is distilled under vacuum (85°-100° C., 3.5 torr) to yield a colorless oil (88.2% yield).

The bromotetrafluoroethyl ether is dehalogenated by combining it with a stoichiometric amount of granular zinc in glyme and refluxing overnight. After removal of the glyme by evaporation, the product, 4-trifluoroethenyloxyanisole, is distilled under vacuum (70° C./2.75 torr, 73% yield). This vinyl ether is cyclodimerized by heating at 195° C. for six hours. The dimerized product, 1,2-bis(4-methoxyphenoxy)hexafluorocyclobutane, is isolated by distillation (120°-130° C./0.05 torr, 91.3% yield).

The bis(methyl ether) is converted to the bis(trimethylsilyl)ether by treatment with four equivalents of trimethylchlorosilane and sodium iodide in refluxing acetonitrile for 48 hours. The bis(trimethylsilyl)ether is then hydrolyzed to the bisphenol by the addition of water, and the bisphenol is extracted with ether. The ether extracts are washed with sodium thiosulfate and concentrated to yield 1,2-bis (4-hydroxyphenoxy)hexafluorocyclobutane as yellowish crystals. The crystals are slurried in methylene chloride, chilled, and filtered to yield white crystals of 1,2-bis(4-hydroxyphenoxy)-hexafluorocyclobutane (73% conversion, 94% yield, with the remainder of the material being 1-(4-hydroxyphenoxy)-2-(4-methoxyphenoxy)hexafluorocyclobutane. Identity of the product is verified using 19F NMR, 1H NMR, and IR spectra. Melting point of the bisphenol is 137°-152° C.

EXAMPLE 3

Preparation of 1,2-Bis(4-Aminophenoxy)Hexafluorocyclobutane by Hoffman Rearrangement of Corresponding Amide 1,2-Bis(4-aminophenoxy)hexafluorocyclobutane is synthesized from 1,2-bis(4-chloroformylphenoxy) hexafluorocyclobutane (of Example 1) by a Hoffman rearrangement of the amide derivative. The diacid chloride is dissolved in methylene chloride and added with stirring to cold concentrated ammonium hydroxide. The diamide begins to precipitate immediately. The slurry is chilled and filtered to yield 1,2-bis(4-carbamoylphenoxy)hexafluorocyclobutane as a white powder (m.p.223°-225° C., quantitative yield).

The diamide is treated with two equivalents of both potassium hypochlorite (0.7 M) and potassium hydroxide at room temperature. After the solids go into solution, the mixture is heated in a 50°-70° C. water bath to effect rearrangement. The resulting diamine is extracted with methylene chloride, concentrated by rotary evaporation and distilled to yield 1,2-bis(4-aminophenoxy)-hexafluorocyclobutane as a yellowish oil.

EXAMPLE 4

Preparation of 1,2-Bis(4-Isocyanatophenoxy)Hexafluorocyclobutane and 1,2-Bis(4-Aminophenoxy)Hexafluorocyclobutane by Curtius Rearrangement from Acid Chloride A sample of 1,2-bis(4-chloroformylphenoxy) hexafluorocyclobutane (5.1 g, 10.8 mmol) prepared as in Example 1, is dissolved in 30 ml of dry acetone and added dropwise to a cold stirring solution of sodium azide (3 g, 46.1 mmol) in 15 ml of water. After addition is complete, the mixture is stirred for 15 minutes, and then diluted with 50 ml of water. The bisazidoformate precipitates as a white powder, which is filtered and dried under vacuum to yield 5.1 g, 97% yield. IR (cm$^{-1}$): 1682 (C=O); 2123, 2163 (N$_3$).

1,2-bis(4-azidoformylphenoxy)hexafluorocyclobutane (4.87 g, 10 mmol) is dissolved in 10 ml of dry toluene and heated to 85°-90° C. under nitrogen until nitrogen evolution has ceased. The mixture is then heated to 110° C. for 40 minutes to ensure complete reaction. The toluene is removed by rotary evaporation to yield 4.3 g of 1,2-bis (4-isocyanatophenoxy)hexafluorocyclobutane (100% yield) as a light brown oil. IR (cm$^{-1}$): 2260 (NCO).

The 1,2-bis(4-isocyanatophenoxy)hexafluorocyclobutane (1.0 g, 2.3 mmol) is dissolved in 5 ml of toluene. Concentrated hydrochloric acid (10 ml) is added, and the mixture is heated to 80° C. for 2.5 hours. The mixture is neutralized and extracted with ether. The ether extracts are concentrated to yield 0.8 g (92% yield) of 1,2-bis(4-aminophenoxy)hexafluorocyclobutane. The product is identified by 19F NMR, 1 H NMR, and IR spectra. IR (cm$^{-1}$): 3400 (NH$_2$).

EXAMPLES 5-14

Preparation and Dimerization of Substituted Phenyl Perfluorovinyl Ethers

For each of Examples 5-14 the following procedure is followed with the details of solvent and reaction temperatures noted in Tables I-III. A phenol starting material having the substituent indicated in Table 1 is dissolved or slurried in methanol to form an admixture. A methanolic solution of one equivalent of potassium hydroxide is added to the stirring admixture. The admixture is cooled to maintain a temperature below 40° C. Stirring and cooling is maintained for about 15 minutes after addition is complete.

The methanol is then removed by rotary evaporation and a resulting wet salt is transferred to a suitable container and dried under vacuum at 100°-140° C. to produce a dry salt. The dry salt is transferred to a dry flask and an equal volume of dry solvent as indicated in Table 1 is added to form a slurry. The flask is fitted with a mechanical stirrer, thermometer, efficient condenser, and pressure-equalizing addition funnel.

The salt slurry is stirred and heated or cooled as indicated in Table 1 as a slight excess (1.1 equivalents) of 1,2-dibromotetrafluoroethane is added slowly. Reaction temperature is dependent on the nature of the substituent group (see Table 1). The reaction temperature is maintained for about 2 hours after addition is complete or until analysis indicates that the phenoxide is consumed and a 2-bromotetrafluoroethyl ether is formed.

The 2-bromotetrafluoroethyl ether is isolated by pouring into an equal volume of water. When the solvent is DMSO, the ether separates as a lower layer of oil and is purified by vacuum distillation. (When the solvent is tetraglyme the product is distilled from the reaction mixture under vacuum.)

TABLE 1

| EX. | Aromatic Substituent | Temp. of Reaction °C. | Heat/Cool | Solvent | Yield % of Theoretical | Product b.p.°C./mm Hg or m.p.* |
|---|---|---|---|---|---|---|
| 5 | —CH$_2$CH$_3$(p) | 25-60 | cool then heat | tetraglyme | 85 | 87/10 |
| 6 | —CH$_2$CH$_3$(m) | 25-90 | cool then heat | tetraglyme | 85 | 75-80/5 |
| 7 | —CH$_3$(p) | 30-70 | cool then heat | tetraglyme | 38 | 85/20 |
| 8 | —C(O)—CH$_3$(p) | 75 | cool then heat | tetraglyme | 27 | 100-115/1 |
| 9 | —H | 20-65 | cool then heat | tetraglyme | 64 | 70-75/20 |
| 10 | —C(O)—OCH$_3$(p) | 65 | heat | DMSO | 85-95 | 85-95/1 |
| 11 | —C(O)—OH(p) | 65 | heat saponification | DMSO | 72 85-100 from ester | 170-173 m.p. |
| 12 | —C(O)—H(p) | 75 | heat | DMSO | 60 | 60-70/1.5 |
| 13 | —BR(p) | 65 | heat | DMSO | 94 | 65/0.15 |
| 14 | —OCH$_3$(p) | 30 | cool | DMSO | 88 | 85-100/3.5 |

*Product boiling points(b.p.) are uncorrected as determined using a Kugelrohr bulb to bulb distillation apparatus and measuring container (oven) temperature. m.p. is melting point in °C.

A perfluorovinyl ether is synthesized by adding the 2-bromotetrafluoroethyl ether into a hot slurry of granular zinc in a dry glyme. When diglyme or tetraglyme is used (as indicated in Table 2) the glymes are about 105°-115° C. when the ether is added. When glyme is used, the bromotetrafluoroethyl ether is combined with granular zinc in dry glyme and refluxed at 85°-90° C. with stirring overnight. The reaction is exothermic and the temperature is regulated by the speed of the addition. For very large reactions the bromotetrafluoroethyl ether is added in portions. This method eliminates the exotherm problem and simplifies product isolation.

After completion of the reaction, the precipitated zinc salts are removed by centrifugation. If diglyme or tetraglyme is used as the solvent, the product is fractionally distilled from the mixture. If glyme is used, the solvent is removed by rotary evaporation and the product is purified by vacuum distillation.

TABLE 2

| Ex. | Phenyl Substituent | Solvent | boiling point °C. (b.p.)/mmHg or melting point(m.p.) | Yield | Comment* |
|---|---|---|---|---|---|
| 5 | —CH$_2$CH$_3$(p) | tetraglyme | b.p. 63/15 | 94 | |
| 6 | —CH$_2$CH$_3$(m) | tetraglyme | b.p. 72/20 | 94 | |
| 7 | —CH$_3$(p) | tetraglyme | 65–70/14 | 75 | |
| 8 | $\overset{O}{\underset{\|}{-C}}$—CH$_3$(p) | tetraglyme | 60–75/0.05 | >60 | similar bp to solvent |
| 9 | —H | tetraglyme | 96/145 | 85 | |
| 10 | $\overset{O}{\underset{\|}{-C}}$—OCH$_3$(p) | tetraglyme | 85–90/8 | 99 | |
| 11 | $\overset{O}{\underset{\|}{-C}}$—OH(p) | glyme | m.p. 139–140 | 99+ | form zinc carboxylate of bromofluoro ether |
| 12 | $\overset{O}{\underset{\|}{-C}}$—H(p) | tetraglyme | purified by chromatography | 80–90 | |
| 13 | —Br(p) | glyme | 40–50/0.25 | 90+ | |
| 14 | —OCH$_3$(p) | glyme | 85–100/3.5 | 73 | |

*b.p. is boiling point

The indicated trifluorovinyl compounds are cyclodimerized by heating to 180°–195° C. for several hours, approximately 6–8 hours. Low boiling impurities and unreacted perfluorovinyl compound are removed by vacuum distillation. The products are distilled under high vacuum and have the characteristics reported in Table 3.

TABLE 3

| Ex. | Phenyl Substituent | m.p. °C. | b.p.°C./mmHg | Yield % | Overall Yield |
|---|---|---|---|---|---|
| 5 | —CH$_2$CH$_3$ (p) | | 110/0.05 | >90 | 35–40% |
| 6 | —CH$_2$CH$_3$ (m) | | 120–130/0.25 | >90 | 35–40% |
| 7 | —CH$_3$(p) | | 90–120/0.05 | >90 | 20% |
| 10 | $\overset{O}{\underset{\|}{-C}}$—OCH$_3$(p) | 67–82 | 135–150/0.025 | 97 | 80% |
| 11 | $\overset{O}{\underset{\|}{-C}}$—OH *(p) | >300 | | 100* prep. from Ex. 10 | 80% |
| 13 | —Br(p) | | 140/0.025 | 95 | 86% |
| 14 | —OCH$_3$(p) | 120– | 91.3–130/0.05 | 59% | |

*prepared by saponification of diester.

EXAMPLE 15

Synthesis of 1,2-Bis(3-Ethynylphenoxy)Hexafluorocyclobutane and 1,2-Bis(4-Ethynylphenoxy)Hexafluorocyclobutane 1,2-Bis(3-ethylphenoxy)hexafluorocyclobutane (204.5 g, 0.0506 mol) (prepared by dimerizing 1-ethyl-3-trifluoroethenyloxybenzene prepared as in Example 6) at 195° C. is transferred to a jacketed 1 L, 3-necked flask fitted with a thermocouple, nitrogen sparger, and magnetic stirrer. A minimum amount (18 mL) of carbon tetrachloride is used to rinse the starting material into the flask. The mixture is stirred and cooled to 0° C.; then cold t-butyl hypochlorite (420 mL, 3.54 mol) is added. The resulting mixture is stirred and cooled to 2° C., then irradiated with a sunlamp while being sparged with a slow stream of nitrogen. The temperature of the reaction is controlled by the amount of irradiation given, and is maintained at 10° to 18° C. overnight. The reaction mixture is then concentrated by rotary evaporation to yield 278.7 g of yellow oil. This oil is added slowly, over 1.5 hours, to a hot (83° C.), stirring mixture of potassium t-butoxide in t-butanol. The reaction mixture is then heated at 78° C. overnight. The mixture is concentrated by rotary evaporation, and partitioned between hexane and water. The hexane solution is separated and dried over 4A molecular sieves, then concentrated to yield 196.5 g of dark brown oil, which is distilled at 130°–140° C./0.05 mmHg to yield 134 g (74% yield from diethyl compound) of viscous, pale yellow oil. The oil is identified as 1,2-bis(3-ethynylphenoxy)-hexafluorocyclobutane by spectra IR, 1H NMR, and 19F NMR. IR (cm$^{-1}$):3300 (acetylenic H), 1H NMR: 3.02 ppm (acetylenic H). The para isomer is prepared from the 1-ethyl-3-trifluoroethenyloxybenzene by the same procedure.

TABLE 4

| Ex. | Phenyl Substituent | m.p. °C. | b.p. °C./mmHg | Yield % | Overall Yield |
|---|---|---|---|---|---|
| 15a | —C≡CH (p) | <60° C. | 110–115/0.05 | 70–80 prep. from Ex. 5 | 32–40% |
| 15b | —C≡CH (m) | | 110–115/0.05 | 70–80 prep. from Ex. 6 | 32–40% |

EXAMPLE 17

Preparation of 4-Trifluoroethenyloxyaniline via the Amide 4-(2-Bromotetrafluoroethoxy)benzoic acid prepared as in Example 18 (26.6 g, 0.083 mol) is transferred to a 250 mL round-bottomed flask along with 150 mL of methylene chloride. Oxalyl chloride (11.64 g, 0.92 mol) is added and the mixture is stirred under nitrogen overnight to form a turbid solution which is concentrated by rotary evaporation and distilled at 80°–90° C./0.1 mmHg to yield 20.88 g of 4(2-bromotetrafluoroethoxy)-benzoyl chloride as a colorless liquid, leaving 6.16 g of unreacted acid (76.8% conversion, 96.5% yield). The benzoyl chloride is added slowly with stirring to 8 mL of cold ammonium hydroxide (0.12 mol). The product amide precipitates as fine white needles which are filtered and dried under vacuum to yield 14.74 g of 4-(2-bromotetrafluoroethoxy)benzamide (75% conversion, 99% yield, m p. 150.5°–151.5° C.), along with 4.8 g of 4-(2-bromotetrafluoroethoxy)benzoic acid which is recovered from the mother liquor (24.3% recovery).

The crystalline amide (10 g, 0.316 mol) is transferred to a 250 mL round-bottomed flask along with 48 mL of cold potassium hypochlorite (KOCl) solution (0.667 M) containing 2 g of potassium hydroxide. The resulting mixture is stirred until most of the solids have dissolved. The mixture is then warmed in a 50°–70° C. water bath to effect the rearrangement to the amine. The mixture is extracted with methylene chloride and the extracts are dried over magnesium sulfate and concentrated by rotary evaporation. The resulting brown oil is distilled at 60°–80° C./0.05 mmHg to yield 4.85 g of 4-(2-bromotetrafluoroethoxy)aniline as a colorless oil (53 3% yield).

A mixture of 4-(2-bromotetrafluoroethoxy)aniline (1.44 g, 5 mmol), dry glyme (15 mL), and zinc (10 mesh, 0.4 g, 5.5 mmol) is formed and stirred with heating to reflux under nitrogen overnight. The mixture is filtered to remove insoluble zinc salts, and then concentrated to yield a cream colored solid material which is found to be the zinc complex of 4-trifluoroethenyloxyaniline.

The product amine is isolated by redissolving the complex in glyme and adding saturated aqueous sodium bicarbonate (NaHCO$_3$) to the solution to precipitate the zinc ion as its bicarbonate salt. The amine is extracted with methylene chloride, dried over sodium sulfate, and distilled at 45° C./0.025 mmHg to yield 0.83 g of 4-trifluoroethenyloxyaniline (88% yield) as a colorless liquid. The product is identified by 19F NMR, 1H NMR, and IR spectra.

EXAMPLE 18

Preparation of Polyesters from 1,2-Bis(4-Chloroformylphenoxy)Hexafluorocyclobutane by Solution Polymerization Methyl 4-hydroxybenzoate (304.3 g, 2 mol) is dissolved in 800 mL of methanol and is converted to the potassium salt by the slow addition of potassium hydroxide (132.02 g, 2 mol, 85% purity). The resulting mixture is stirred and cooled as necessary to maintain the temperature below 50° C. The solvent is then removed by rotary evaporation and the crystalline salt is dried under vacuum overnight at 140° C.

The dried salt is allowed to cool and transferred to an oven dried 2 L flask under nitrogen. The flask is fitted with a mechanical stirrer, thermometer, heating mantle, condenser and pressure-equalizing addition funnel. Dry dimethylsulfoxide (DMSO) (550 g) is added and the mixture is stirred and warmed to 60° C. as 1,2-dibromotetrafluoroethane (537 g, 2.06 mol) is added slowly. (No appreciable reaction is observed at lower temperatures.) Reaction temperature is maintained at 65°–70° C. for two hours after addition is complete. The mixture is then heated to 90° C. and allowed to cool overnight.

Product is isolated by extracting the mixture with 500 mL of water to remove salts and DMSO. The product separates as an orange oil which is washed with water to remove residual DMSO. (The upper aqueous layer is extracted with methylene chloride and the methylene chloride solution is evaporated to yield about 40 g of product which is added to the rest of the product prior to the water washes.) The product (623 g) is distilled at 85° C./0.3 mmHg to yield 561 g of colorless oil, 85% yield. The product, methyl 4-(2-bromotetrafluoroethoxy)benzoate, is identified by 19F NMR, 1H NMR, and IR spectra.

To form the benzoic acid, methyl 4-(2-bromotetrafluoroethoxy)benzoate (33.11 g, 0.1 mol) is weighed into a 250 mL round-bottomed flask along with potassium hydroxide (85%, 8.77 g, 0.13 mol), water (5 mL) and methanol (100 mL). The mixture is stirred overnight and then acidified by the addition of 16 mL of concentrated hydrochloric acid. Product, 4-(2-bromotetrafluoroethoxy)benzoic acid, precipitates as white flocculent crystals. The methanol is removed by rotary evaporation and the product is dissolved in methylene chloride and washed with water. The methylene chloride solution is dried over magnesium sulfate, filtered and concentrated to yield 28.66 g of white crystals (yield 90.4%, m.p.170°–173° C.). The product is identified by 19F NMR, 1H NMR, and IR spectra.

To form a salt suitable for formation of the perfluorovinyl ether, another sample of methyl 4-(2-bromo-tetrafluoroethoxy)benzoate (66.25 g, 0.2 mol) is weighed into a 4-necked 500 mL round-bottomed flask fitted with a condenser, thermometer, mechanical stirrer, and heating mantle. Methanol (300mL) and sodium hydroxide (8.05 g, 0.2 mol) are added to form a mixture which is stirred and heated to reflux for three hours. A sodium carboxylate forms and begins to precipitate early in the reaction and is gelled into an almost solid mass after 1.5 hours. The mass is allowed to settle overnight and the solvent is then removed by rotary evaporation.

The sodium carboxylate is dissolved in warm water. A warm solution of zinc acetate (26.35 g, 0.12 mol) in 40 mL of water is added to precipitate the carboxylate as the zinc salt. The salt slurry is then cooled, and the zinc salt is filtered from the solution and dried under vacuum to yield 65.6 g (94% yield).

The dried zinc salt is transferred to a dry 4-necked 500 mL round-bottomed flask containing zinc metal (10 mesh, 13.0 g, 0.198 mol). Dry glyme (160 mL) is added by a canula and the flask is fitted with a condenser, mechanical stirrer, and thermometer. The mixture is stirred and heated to reflux under nitrogen overnight. The mixture is acidified by the addition of 18 mL of concentrated hydrochloric acid (HCl), concentrated by rotary evaporation, and then partitioned between methylene chloride and water. The methylene chloride solution of the acid is dried over magnesium sulfate, filtered and concentrated to yield 40.02 g of 4-trifluoroethenyloxybenzoic acid as white crystals (97.6% yield, m.p. 139°–140° C.). The product 4-trifluoroethenyloxybenzoic acid is identified by 19F NMR, 1H NMR, and IR spectra.

To form the 4-trifluoroethenyloxybenzoyl chloride, 4-trifluoroethenyloxybenzoic acid (79.4 g, 0.36 mol) is transferred to a 1 L round-bottomed flask. Dry methylene chloride (250 mL) is added, and the resulting mixture is stirred under nitrogen as oxalyl chloride (62.5 g, 0.49 mol) is added. The mixture is stirred overnight and then concentrated by rotary evaporation. The brown liquid is distilled at 60°–65° C./0.2 mmHg to yield 82.94 g of colorless liquid (97.4% yield). The product is identified by 19F NMR, 1H NMR, and IR spectra.

Bisphenol AP (1,1 bis(4-hydroxyphenyl)-1-phenylethane) (6.14 g, 21.1 mmol) is transferred to a dried resin kettle (a reaction vessel with a large top that clamps onto the vessel) along with 50 mL of dry dichloromethane. The mixture is stirred under nitrogen as triethylamine (5.9 mL, 42.2 mmol) is added via syringe. The solution is stirred and cooled in a water bath as a solution of 1,2-bis(4-chloroformylphenoxy) hexafluorocyclobutane (as prepared in Example 1) (10.Gg, 21.1 mmole) in dichloromethane (50 mL) is added via syringe. The mixture is allowed to stir overnight under nitrogen to form a polymer in solution.

The polymer is then capped by adding 0.25 mL of 4-trifluoroethenyloxybenzoyl chloride to the solution with stirring. The solution is diluted with 200 mL of dichloromethane and washed with water to remove triethylamine hydrochloride until a sample of the water washes added to a 5% silver nitrate solution produces no silver chloride precipitate. The polymer solution is then poured into a glass dish, and the dichloromethane is allowed to evaporate overnight, leaving a clear, tough film, which is dried under vacuum at 140° C. and is weighed. (Yield=14.58 g, 99.9%)

EXAMPLE 19

Preparation of Polyesters from 1,2-Bis(4-Chloroformylphenoxy)Hexafluorocyclobutane by Emulsion Polymerization Bisphenol AP (10.51 g, 36 mmol) is transferred to a blender container along with water (200 mL), 50% aqueous sodium hydroxide (6.6 g, 82 mmol) and benzyltrimethylammonium chloride (2 g, 6.5 mmol, 60% aqueous solution). Agitation is supplied by a blender plugged into and having its speed controlled by a Variac. The mixture is agitated at 25-30% power until the bisphenol AP dissolves.

1,2-bis(4-chloroformylphenoxy)hexafluorocyclobutane (prepared as in Example 1) (17.12 g, 36 mmol), is dissolved in 70 mL of dichloromethane to form a diacid chloride solution and is chilled in an ice bath. Dichloromethane (25 mL) is added to the blender, which is agitated at 30% power for 2 minutes, at which time the chilled diacid chloride solution is added to the blender over a period of 20 seconds to form an admixture. The container in which the diacid chloride mixture is chilled is rinsed with 30 mL of dichloromethane, which is added to the admixture. The admixture is agitated at 40% power for 12 minutes; then 1.2 mL of benzoyl chloride is added. The admixture is agitated for an additional 2 minutes. Then aggitation is stopped and layers are allowed to separate. An aqueous layer is decanted, and a lower, dichloromethane layer, is agitated with 200 mL portions of deionized water until a sample of the water tests negatively for chloride ion.

Addition of an equal volume of isopropyl alcohol to the volume of dichloromethane layer precipitates a polymer from the dichloromethane solution as a thick, viscous mass. The polymer is allowed to air dry, then redissolved in dichloromethane to form a clear solution and poured into a glass dish. Evaporation of the dichloromethane overnight yields a tough clear film which is dried under vacuum at 140° C. Weight of recovered polymer is 24.56 g, 98% yield.

EXAMPLES 20-25

Polyesters prepared using 1,2-Bis(4-Chloroformylphenoxy)Hexafluorocyclobutane

The process of Example 18 for the solution preparations and the process of Example 19 for the emulsion preparations are repeated using the following bisphenols with the results indicated in the following table, which includes polymers of Examples 18 and 19 for comparison:

| Ex. No. | Bisphenol** | Yield (%) | Tg (°C.) | molecular weight | polymerization method | dielectric constant/dissipation factors at 1 kHz |
|---|---|---|---|---|---|---|
| 20 | Bisphenol A | 100 | 137 | 47000 | solution | 2.93/0.0031 |
| 18 | Bisphenol AP | 99.9 | 178 | 60000 | solution | 3.05/0.0042 |
| 21 | Bisphenol AF | 97 | 160 | 66000 | solution | 2.94/0.0036 |
| 22 | 4,4'-Bisphenol | 98 | >400 | — | solution | * |
| 23 | Hydroquinone | 99 | >400 | — | solution | * |
| 24 | Bisphenol A | 100 | — | 64000 | emulsion | — |
| 19 | Bisphenol AP | 98 | 185 | 104000 | emulsion | — |
| 25 | Bisphenol AF | 100 | — | 79000 | emulsion | — |

*These materials are highly crystalline and precipitate from the reaction mixture. Molecular weights cannot be determined by GPC due to insolubility.
**Bisphenol AF is 2,2-bis(4-hydroxyphenyl)-hexafluoropropane; Bisphenol A is 2,2-bis(4-hydroxyphenyl)propane.

Tensile and flexural strength are determined for a sample of the bisphenol A polymer prepared by solution polymerization (Example 20).
Tensile strength is 6460 pounds/square inch.
Flexural strength is 3060 pounds/square inch.
Flexural Modulus is 330,000 pounds/square inch.

EXAMPLE 26

Polymerization of 1,2-Bis(4-Ethynylphenoxy)Hexafluorocyclobutane

A 5 g sample of 1,2-bis(4-ethynylphenoxy)hexafluorocyclobutane (as prepared in Example 15b) is thermally cured at 180° C. for 3 hour followed by a postcure at 250° C. for 30 minutes. The density of the polymer is 1.34 g/cc. The dielectric constant of the polymer is 2.6 at 1 kHz.

DSC analysis of 1,2-bis(4-ethynylphenoxy) hexafluorocyclobutane indicates a broad exotherm starting at 160° C. and ending at 280° C. with delta H=632 Joules/g. The initially colorless oil turns into a clear, dark red solid which is analyzed by DSC, TMA, and TGA (Thermogravimetric analysis). TGA (20° C./min., nitrogen sweep) of the cured sample shows: 2% loss at 400° C., 5% loss at 470° C., 35% loss at 580° C., and 80% loss at 900° C. No Tg is observed up to 350° C. by DSC or TMA.

EXAMPLE 27

Synthesis of 4-Trifluoroethenyloxyphenyl Acetate from Hhydroquinone Monoacetate, Dimerization of the Phenyl Acetate and Conversion to the Corresponding Phenol Hydroquinone monoacetate (205.4 g, 1.35 mol), available from p-isopropylphenyl acetate by the method of Van Sickle (*Ind. Eng. Chem. Res.*, 27. 440–447 (1988)), is dissolved in 800 mL of methanol and cooled to less than 10° C. with stirring. A solution of potassium hydroxide (90.9 g, 1.38 mol) in 200 mL of methanol is added slowly with cooling, keeping the reaction temperature below 20° C. The mixture is stirred for 30 minutes, then concentrated by rotary evaporation. The resulting wet salt is transferred to a crystallizing dish and dried overnight under vacuum at 120° C. The resulting dry salt is transferred to a dry 2 L, 4-necked flask fitted with a mechanical stirrer, thermometer, condenser, and pressure-equalizing addition funnel. Dry DMSO (520 g) is added to form a reaction mixture which is stirred and cooled to 10° C. The reaction mixture is stirred and maintained at 10°–20° C. as 1,2-dibromotetrafluoroethane (421 g, 1.62 mol) is added slowly. After addition is complete, the mixture is heated to 60° C. for 1 hour, cooled and poured into an equal volume of water.

Product, 4-(2-bromotetrafluoroethoxy)phenyl acetate is separated as an oily lower layer, which is washed with water to remove residual DMSO, dried over 4A molecular sieves, and distilled under vacuum (85° C./0.5 torr) to yield product 4-(2-bromotetrafluoroethoxy)phenyl acetate as a colorless oil (60–85% yield).

The product is dehalogenated by combining it with 1–2 volumes of dry glyme as solvent and 1–1.1 equivalents of zinc and refluxing with stirring overnight. The solvent is then removed by rotary evaporation, and resulting product and zinc salts are slurried in hexane or dichloromethane. The zinc salts are removed from the product by filtration, and the product 4-trifluoroethenyloxyphenyl acetate is isolated by vacuum distillation at 70°–80° C./3 torr to give the purer product as a colorless oil.

4-Trifluoroethenyloxyphenyl acetate is dimerized to 1,2-bis(4-acetoxyphenoxy)hexafluorocyclobutane by stirring and heating to 195° C. for 6–8 hours. The product is distilled under vacuum to yield 1,2-bis(4-acetoxyphenoxy)hexafluorocyclobutane as a low melting crystalline solid (m.p. 60°–80° C.).

1,2-Bis(4-acetoxyphenoxy)hexafluorocyclobutane is converted to 1,2-bis(4-hydroxyphenoxy)hexafluorocyclobutane by treatment with two molar equivalents of sodium hydroxide in methanol. The methanol is removed by rotary evaporation, and a product bisphenol is dissolved in ether, washed with water, dried over 4A molecular sieves, and concentrated to yield 1,2-bis(4-hydroxyphenoxy)hexafluorocyclobutane.

What is claimed is:

1. A compound having at least one perfluorocyclobutane ring and at least two reactive functional groups and a structure represented by Formula II:

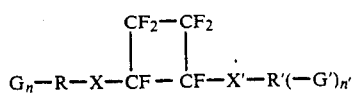

wherein R and R' independently represent optionally inertly substituted groups: X and X' represent any molecular structures which link R an R' with the perfluorocyclobutane ring; n and n' are the number of G and G' groups, respectively; and G and G' independently represent any reactive functional groups or any groups convertible into reactive functional groups, and wherein R represents an unsubstituted or inertly substituted aromatic hydrocarbyl group, or X represents a group selected from the group consisting of oxygen atoms, sulfur atoms, sulfoxide, sulfone, carbonyl, and thiocarbonyl groups.

2. A compound having from about 2 to about 50 perfluorocyclobutane groups, and at least two reactive functional groups.

3. The compound of claim 2 having from about 2 to about 25 perfluorocyclobutane groups.

4. The compounds of claim 1 having a structure represented by Formula II:

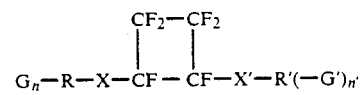

wherein R and R' independently represent optionally inertly substituted groups; X and X' represent any molecular structures which link R and R' with the perfluorocyclobutane ring; n and n' are the number of G and G' groups, respectively; and G and G' are independently selected from the group consisting of functional groups including hydroxyl groups (both alcoholic and phenolic) and esters thereof, carboxylic acid groups, acyl halides, isocyanates, acetyl groups, trihaloacetyl groups, sulfide groups, sulfonic acid groups, sulfonamide groups, ketones, aldehydes, epoxy groups, primary or secondary amides, nitro groups, anhydrides, imides, phosphines, phosphate, phosphonate, and boranes.

5. The compounds of claim 4 wherein n and n' are each integers of from 1 to about 4.

6. The compounds of claim 5 wherein n and n' are independently integers from 1 to about 2.

7. The compounds of claim 6 wherein n and n' are each 1.

8. The compounds of claim 6 wherein X and X' are independently selected from linking structures such as bonds, oxygen atoms, carboxylic and thiocarboxylic ester groups, sulfides, sulfones, perfluoroalkylenes, perfluoroalkylene ethers, alkylenes, acetylenes, phosphines, carbonyl and thiocarbonyl groups; seleno; telluro: nitrido (N→O), silanediyl, trisilanediyl, tetrasilanetetrayl, siloxanediyl, disiloxanediyl, trisiloxyl, trisilazanyl, or silylthio groups; boranediyl or methylboranediyl groups; or a combination thereof.

9. The compounds of claim 8 wherein X and X' are the same and are oxygen or sulfur groups.

10. The compound of claim 8 wherein R and R' are independently unsubstituted or inertly substituted hydrocarbyl groups having a molecular weight of from about 14 to about 20,000.

11. The compound of claim 10 wherein R and R' are the same and are aliphatic, cycloaliphatic, aromatic or heterocyclic.

12. The compound of 10 wherein at least one of X', R', or G' is different from the corresponding X, R or G.

13. The compound of claim 8 wherein G and G' are independently selected from the group consisting of hydroxyl groups (both alcoholic and phenolic) and esters thereof, thiocarboxylic and carboxylic acid groups, acyl halides such as chlorides, isocyanates, acyl azides, acetyl groups, trihaloacetyl groups, primary or secondary amines, sulfide groups, sulfonic acid groups, sulfonamide groups, ketones, aldehydes, epoxy groups, primary or secondary amides, halo groups, nitro groups, cyano groups, anhydrides, imides, cyanate groups, vinyl, allyl, acetylene groups; silicon-containing substituents, phosphorus-containing groups, boron-containing groups, esters including thiocarboxylic and carboxylic esters; trihalomethyl groups including trichloromethyl groups, alkoxy groups; when R is aromatic, alkyl groups.

14. The compound of claim 13 wherein G and G' are independently selected from hydroxyl and esters thereof, carboxylic or thiocarboxylic acid ester groups, carboxylic acid groups, acyl chlorides, isocyanates, acetylene groups, alkoxy groups, alkyl groups when R is aromatic, and primary or secondary amines.

15. The compound of claim 14 wherein R and R' are aromatic groups.

16. The compound of claim 15 wherein X and X' are the same and are oxygen or sulfur groups.

17. The compound of claim 16 wherein X and X' are oxygen.

* * * * *